(12) United States Patent
Friess et al.

(10) Patent No.: US 8,372,895 B2
(45) Date of Patent: Feb. 12, 2013

(54) BIOMATERIAL CONTAINING DEGRADATION STABILIZED POLYMER

(75) Inventors: Wolfgang Friess, Iffeldorf (DE); Klaus Hellerbrand, Moorenweis (DE); Samuel Herberg, Augusta, GA (US); Cornelius Pompe, Munich (DE); Andreas Schuetz, Stockdorf (DE); Michael Siedler, Munich (DE)

(73) Assignee: Scil Technology GmbH, Martinsried (DE)

( * ) Notice: Subject to any disclaimer, the term of this patent is extended or adjusted under 35 U.S.C. 154(b) by 286 days.

(21) Appl. No.: 12/305,333

(22) PCT Filed: Jun. 28, 2007

(86) PCT No.: PCT/EP2007/005752
§ 371 (c)(1),
(2), (4) Date: Feb. 9, 2009

(87) PCT Pub. No.: WO2008/000488
PCT Pub. Date: Jan. 3, 2008

(65) Prior Publication Data
US 2009/0209660 A1 Aug. 20, 2009

(30) Foreign Application Priority Data
Jun. 30, 2006 (EP) .................................. 06013646

(51) Int. Cl.
*A61K 47/30* (2006.01)
*A61F 2/00* (2006.01)
*C08K 3/10* (2006.01)
*C08K 3/30* (2006.01)
*C08K 3/34* (2006.01)

(52) U.S. Cl. ..... 523/113; 424/423; 433/215; 514/772.3; 524/423; 524/442

(58) Field of Classification Search .................. 523/113; 524/423; 424/423; 433/215
See application file for complete search history.

(56) References Cited

U.S. PATENT DOCUMENTS

| | | | |
|---|---|---|---|
| 4,853,211 A * | 8/1989 | Kurobe et al. | 424/433 |
| 6,231,970 B1 * | 5/2001 | Andersen et al. | 428/332 |
| 2002/0044968 A1 | 4/2002 | van Lengerich | |
| 2002/0081358 A1 | 6/2002 | Galland et al. | |
| 2003/0021973 A1 * | 1/2003 | Topolkaraev et al. | 428/220 |
| 2004/0018238 A1 * | 1/2004 | Shukla | 424/486 |
| 2004/0173779 A1 * | 9/2004 | Gencer et al. | 252/387 |
| 2005/0106214 A1 * | 5/2005 | Chen | 424/426 |
| 2005/0251149 A1 * | 11/2005 | Wenz | 606/94 |
| 2005/0251266 A1 * | 11/2005 | Maspero et al. | 623/23.51 |
| 2006/0204586 A1 * | 9/2006 | Alexander et al. | 424/489 |
| 2008/0063681 A1 * | 3/2008 | Simon et al. | 424/423 |

FOREIGN PATENT DOCUMENTS

| | | |
|---|---|---|
| EP | 0 442 680 A1 | 8/1991 |
| EP | 0 856 534 A1 | 8/1998 |
| EP | 1 344 538 A1 | 9/2003 |
| EP | 1 462 130 A1 | 9/2004 |
| JP | 10-101465 * | 4/1998 |
| JP | 10101465 * | 4/1998 |
| JP | 10-165733 * | 6/1998 |
| JP | 10165733 A * | 6/1998 |
| JP | 2004-536685 A | 12/2004 |
| JP | 2005-519676 A | 7/2005 |
| JP | 2007-534449 A | 11/2007 |
| WO | WO 01/32072 A2 | 5/2001 |
| WO | WO 03/011957 A1 | 2/2003 |
| WO | WO 2005/105170 A1 | 11/2005 |
| WO | WO 2005/120595 A2 | 12/2005 |
| WO | WO 2010/080896 A2 | 7/2010 |

* cited by examiner

*Primary Examiner* — Tae H Yoon
(74) *Attorney, Agent, or Firm* — Leydig, Voit & Mayer, Ltd.

(57) ABSTRACT

The present invention relates to a polymer based material comprising a water binding agent, whereas the water binding agent is present in an amount sufficient to chemically and/or physically absorb and/or adsorb water to prevent degradation of the polymer. It also relates to a polymer based material which comprises a plasticizer or organic solvent as well as a multi-component material or composite including materials encompassing a second polymer and/or an active agent. Furthermore it relates to a method for manufacturing the polymer comprising material and use of the material for the preparation of a pharmaceutical composition to be used for treatment of bone, cartilage and/or periodontal defects. The invention also encompasses a kit using the polymeric material. Further, the present invention encompasses the use of a water binding agent for inhibiting water induced degradation of a polymer comprising material, for inducing blood clot stabilization in a polymer comprising material and for increasing storage stability in a polymer comprising material, wherein the water binding agent is not removed prior to application of the material.

12 Claims, 7 Drawing Sheets

BIOMATERIAL CONTAINING DEGRADATION STABILIZED POLYMER

BACKGROUND OF THE APPLICATION

Technology of absorbable or biodegradable polymers has evolved in many areas over the last years. This is because tissue engineering relies, for the most part, on the use of absorbable scaffold that undergoes mass loss in tandem with tissue formation to replace the absorbing scaffold. While playing a significant role as implants for tissue regeneration especially in bone and cartilage regeneration in extruded and molded solid forms, absorbable polymers are increasingly used in moldable or injectable liquids and gels including suspensions, dispersions and hydrogels.

Many bioabsorbable biomedical polymers rely on the hydrolytic instability of the polymer. Preferably polyester linkage hydrolysis is the responsible mechanism for their in vivo degradation in such polymers (Absorbable and biodegradable polymers, Shalaby and Burg 2004. CRC Press, Advance in polymeric biomaterial series. Chapter 9.5.3).

One major drawback of materials comprising such polymers like poly-L-lactide (PLLA), poly-L-lactic-co-glycolic acid (PLGA), copolymers of PLGA and polyethylene glycol (PEG) polymers is their short shelf-life and storage instability. Already traces of water induce degradation during long term storage and before application of the polymer based material, which might result in undesired features such as segmentation, sedimentation, decomposition, alteration of the viscosity of liquid biomaterials, alteration of the scaffold properties and/or an altered degradation profile in vivo and possible unpredictable results.

WO 2005/105170 discloses a bone substitute material of two components, namely a mineral component and a non-aqueous component, which hardens in an aqueous environment by replacing the non-aqueous component with water. The mineral component e.g. calcium sulfate dihydrate or calcium sulfate hemihydrate disclosed in the bone substitute material functions as a seed which enables to form a cement which strong mechanical properties lacking macroporosity.

In order to overcome this drawback, so far employed conventional methods aim at easy and low cost procedures. One approach employs heating of the used ingredients either alone or in the presence of a catalyst to reduce the water content of the composition.

Also treatment with a drying agent and subsequent removal of the drying substance or distillation of solvents such as organic solvents, treating distilled solvents with a drying agent and returning the treated solvent to the system are commonly used as well as distilling out water, binding the distilled water of a solvent with a drying agent and returning the so obtained substance like the solvent to the system.

Alternatively, waterproof packages with or without water drying external agents or dessicants, preferably packages made of plastics and aluminium including blister packages particularly those with a reduced water vapor permeability are a preferred packaging form for solid or semi-solid and liquid pharmaceutical preparations which are moisture sensitive as is e.g. described in EP 0 779 872 and references therein incorporated by reference herewith.

However, in order to prepare and to maintain water free polymer based materials such as liquid polymer solutions, polymer dispersions, polymer melts and liquid polymer based materials, known methods including thermal pretreatment of ingredients, vacuum drying, lyophillisation, molecular sieve as well as using a packaging system with desiccants for packaging moisture sensitive pharmaceutical preparations have been unsuccessful. Further improvements have been required for the step of avoiding polymer degradation upon storage of the material by removing water from the composition.

Accordingly, it is one object underlying the present invention to provide alternative means to prepare and to maintain water free polymer based materials (i.e. materials comprising polymers such as liquid polymer solutions, polymer dispersions, polymer melts and liquid polymer based materials).

Moreover, it is another object underlying the present invention to provide alternative means for inhibiting water induced polymer degradation in a polymer based material, which means preferably increase storage stability in a polymer comprising material such as liquid polymer solutions, polymer dispersions, polymer melts and liquid polymer based materials.

Furthermore, it is another object underlying the present invention to provide means for inhibiting of water induced polymer degradation in a polymer based material, which can be applied in cases, wherein conventionally used methods as listed above are not suitable, cumbersome, expensive or laborious.

Alternatively, the object underlying the present invention was to provide a polymer comprising material exhibiting improved shelf-life time, in which the degradation of the polymer is prevented or inhibited during storage, i.e. before use.

Another object underlying the present invention was to provide a polymer comprising material exhibiting improved shelf-life time for tissue regeneration, which forms a sponge-like matrix.

Another object underlying the present invention was to provide a polymer comprising material with increased shelf-life time for tissue regeneration including periodontal attachment or tissue regeneration.

Another object underlying the present invention was to provide a material for inducing blood clot formation or blood clot stabilization.

Another object underlying the present invention was to provide a polymer comprising material for periodontal tissue regeneration and a method for using it.

SUMMARY OF THE INVENTION

As a result of an intensive investigation in order to overcome this problem and to improve the process as to more efficient and less cost intensive prepare a polymer comprising material, the present inventors have surprisingly found that the use of a water binding agent within the material without removing it from the formulation after water binding is effective for inhibition of polymer degradation during long term storage.

Accordingly, the present invention provides a polymer comprising material such as liquid polymer solutions, polymer dispersions, polymer melts and liquid polymer based materials comprising a water binding agent, wherein the water binding agent is present in an amount sufficient to physically absorb and/or adsorb or chemically adsorb water to prevent degradation of the polymer.

One advantage resulting from the addition of the water binding agent is the inhibition of sedimentation and phase separation, respectively, of the obtained polymer comprising material.

A preferred aspect of the present invention regards particular polymer based compositions, which comprise the polymer component in liquid or solved form. Sometimes organic solvents or so-called plasticizers are used to dissolve the polymer or keep the polymer in the liquid phase, preferably in solution. Unfortunately such systems show a particularly poor storage stability and can hardly be stored over many weeks particularly when the organic solvent is hygroscopic or can even bind up to 50% of water of its own weight such as polyethylene glycol 400. Such liquid polymer based materials are much more sensitive to polymer degradation than solid polymer materials. One example of such a polymer based material is a material comprising a poly(-lactic-co-glycolic-acid) polymer (Resomer® RG503H of Boehringer Ingelheim) dissolved in polyethylenglycol 400 as described in Example 12 of the present invention.

Therefore, there is a particular need for stabilizing polymer comprising materials comprising the polymer in liquid phase. Such materials include, but are not limited to moldable and injectable polymer comprising materials and preferably fast degrading polymer comprising materials, wherein cleavage is due to water induced hydrolysis of the polymer chain such as the ester group of the polymer chain (e.g. polyester).

In particular in the case of hygroscopic liquids, including but not limited to organic solvents such as polyethylengylcol (e.g. polyethylengylcol 300) or N-methyl-pyrrolidone, which can be used for example in in situ forming polymer based biomaterials, e.g. in implants or pharmaceutical formulations, long-term storage stability has been a tremendous problem.

A further aspect of the present invention is, hence, to provide a polymer comprising material comprising a polymer in liquid phase, which can be stored for a long time e.g. without or with limited polymer degradation or polymer chain cleavage. Preferably such material maintains its mechanical and functional stability.

The inventors found that traces of water within polymer containing liquids can even more damage the polymer via water-induced hydrolysis (i.e. chain cleavage) than in solid materials such as solid implants.

Moreover, such traces are not removed with conventional drying methods.

Due to the addition of the water binding agent in an amount sufficient to physically or chemically absorb and/or adsorb water that can not be removed by classical drying procedures such as described above to prevent or limit the degradation of the polymer, a polymer comprising material comprising a pharmaceutical acceptable plasticizer such as an organic solvent could be prepared, wherein the degradation of the polymer was significantly inhibited or reduced. Thereby a significant increase in shelf-life time of the material was achieved without a negative influence on the function of the material such as scaffold properties of the material for example after in situ formation.

In this aspect of the invention, the inventors provide a polymer comprising material comprising a water binding agent, wherein the water binding agent is present in an amount sufficient to physically or chemically absorb water to prevent degradation of the polymer, wherein the material comprises a plasticizer, preferably a pharmaceutical acceptable plasticizer or organic solvent.

The inventors surprisingly found that beside the inhibition of polymer degradation also the morphology of biomaterials or pharmaceutical preparations and the mechanical properties of the biomaterials or pharmaceutical preparations were also improved. For example the addition of only approximately 4% of the water binding agent (e.g. calcium sulfate as shown in FIG. 3) leads to a significant increase of the mechanical strength over storage time compared to a material without the water binding agent.

In addition, the inventors surprisingly found that in the case of a water binding agent comprising a calcium compound such as calcium sulfate anhydrous or semihydrate, biomaterials exhibiting further synergizing effects could be produced. Upon implanting a biomaterial, the coagulation cascade was induced leading to an intimate binding between the blood clot and the porous matrix of the biomaterial (shown in FIG. 4), which improves tissue regeneration. Furthermore, the material of the invention preferably has growth factor binding activity and is able to entrap or immobilize one or more growth factors from the surrounding tissue after implantation.

In another embodiment, the inventors provide a polymer comprising material of any of the embodiments, which is a non-solid material in a non-aqueous environment, wherein upon in situ formation the polymer forms a matrix and said water binding agent is settled within the matrix. Preferably, the polymer comprising material of the above embodiment almost remains its geometry upon in situ formation in an aqueous environment.

In another preferred aspect of the present invention, the inventors provide a polymer comprising material comprising additional components, e.g. an inorganic filler, a pore forming agent, a pore initiating filler or at least a second polymer or any combination thereof.

So far biomaterials comprising a polymer and a plasticizer together with additional components such as an inorganic filler or a pore forming agent or combinations thereof are known from WO 05/120595 filed by the present inventors.

For these multi-component materials such as of WO05/120595 the inventors found that there is a risk of degradation or alteration of the polymer chain during long term storage and a need for further improvement of the stability of the product, i.e. before the materials are used or applied to a tissue.

The present inventors identified that water, either chemically bound or physically entrapped in the system can be introduced into the material by several components and is freed during long term storage. It was further found that drying of individual components and subsequently manufacturing the multi-component material was difficult as well as cost intensive and needed further improvement to allow for a long term storage over many weeks or month preferably a year or even longer. It was particularly intended to provide new means for increasing shelf-life and to minimize or inhibit the probability of degradation during storage periods over 4 weeks or more.

Surprisingly, however, these limitations were overcome by addition of a water binding agent, which water binding agent is not present in the composition of WO 05/120595.

Even in the case of using acidic or basic additives or excipients such as drugs, basic or acidic inorganic compounds, the shelf-life of the materials is extended, because of the reduced content of water which is chemically bound or physically absorbed and/or adsorbed within the material by the water binding agent.

Hence, in this aspect of the invention a polymer comprising material comprising an inorganic filler, a pore forming agent, a pore initiating filler or at least a second polymer or any combination thereof together with a water binding agent, wherein the water binding agent is present in an amount sufficient to physically or chemically absorb and/or adsorb water to prevent degradation of the polymer, is provided.

A further aspect of the invention is the use of a pore initiating filler such as mannitol in a polymer based material, preferably an in situ hardening biomaterial.

The pore initiating filler like mannitol rapidly introduces an initial porosity of the material. This initial porosity of small pores or cavities enables to achieve a guided formation of the final overall porous structure of the material by a second pore forming agent such as a swelling agent (e.g. carboxymethylcellulose). This surprising effect leads to the formation of a highly sponge-like material with interconnecting pores as shown in FIG. 5.

In addition, mannitol has the advantage that it is also usable as a bulking agent for active agent formulations such as an active agent lyophilizate as used in Example 3.

Preferably, the pore initiating filler is an organic water soluble substance, more preferably an alcohol or polyalcohol such as mannitol.

An advantage of the second polymer such as the water soluble solid polymer (e.g. PEG 1500) is that it has a long lasting plasticizing effect on the first polymer such as PLGA. One example is illustrates in Example 4 and FIG. 5 of the present invention. While the pore forming process due to the pore forming agent such as the swelling agent like carboxymethylcellulose needs time to be completed while the material hardens in situ a long lasting placticizer remains a moldable appearance of the polymer to achieve the interconnecting sponge-like porosity suitable for tissue regeneration such as periodontal regeneration or bone defect filling (see the sponge-like structure of FIG. 5).

Particularly good results have been observed by using less than 8 wt % of the second polymer, preferably less than 5 wt %, more preferably less than 3 wt % and most preferably between 1 and 2.5 wt %. Preferably, the polymer comprising material of any of the above embodiments, comprises a second polymer, wherein the second polymer is a water insoluble solid polymer.

Another aspect of the present invention is to provide a material of any one of the above embodiments such as a liquid polymer solution comprising a first plasticizer, a pore forming agent and a second plasticizer, wherein preferably the second plasticizer is a second polymer preferably solid polymer preferably with a molecular weight of 1000 or more or an antioxidants, preferably a lipid soluble antioxidants, which is soluble in an organic solvent and/or liquid polymer. Preferably the antioxidans is tocopherol, methionin, butylhydroxytoluol, butyl 4-hydroxyanisol, more preferably alpha-tocopherol. Preferably the second plasticizer is biocompatible.

The function of the second plasticizer is to increase the glas transition temperature ($T_g$) of the polymer such as the PLGA solution. Preferably, the final material has a $T_g$ between 0° C. and −56° C., more preferably of about −50° C.±6° C. The $T_g$ can be determined as for example described in Example 13.

Surprisingly, the inventors found that an antioxidant such as tocopherol functions as a plasticizer when added to the polymer comprising material of the present invention. Particularly good results have been observed by using less than 5 wt %, more preferably about or less than 3 wt %, most preferably between 1 and 2.5 wt %. Contrary to what was expected, the addition of the solid polymer (e.g. PEG 1500) or the antioxidants (e.g. alpha-tocopherol) especially in the preferred amount did not negatively influence the in situ hardening of the polymer based material.

TABLE 1

Glass transition temperatures of different polymers and polymer compositions (n = 2)

| Sample | Tg [° C.] |
|---|---|
| PEG 300 | −73.6 |
| PLGA 502H | +47.3 |

TABLE 1-continued

Glass transition temperatures of different polymers and polymer compositions (n = 2)

| Sample | Tg [° C.] |
|---|---|
| a-Tocopherol | −31.7 |
| PEG 300 + PLGA 502H | −61.9 |
| PEG 300 + PLGA 502H + PEG 1500 (2 wt %) | −55.8 |
| PEG 300 + PLGA 502H + a-Tocopherol (2 wt %) | −54.1 |

Another aspect of the present invention is to provide a material of any one of the above embodiments comprising an active agent. The active agent is not limited to bone morphogenetic proteins or periodontal ligament, cementum and/or alveolar bone inducing agents such as members of the TGF-superfamily, BMPs and GDFs or combinations thereof.

The inventors have successfully analyzed the biocompatibility of the material of Example 2 in a preclinical one-wall intrabony periodontal defect model in beagle dogs.

Histologic and histometric observations revealed excellent biocompatibility of the material. Due to the carefully chosen formulation of the material no inflammatory lesions in sites implanted with the biomaterial were observed, which was described to be a disadvantage of several known biodegradable polymer based implants in the literature (e.g. biodegradable membranes used for periodontal defects). Unexpectedly, GDF-5 lead to a regeneration of cementum and alveolar bone formation of the periodontal attachment apparatus. Even more, ligament formation was induced.

Due to the present invention the self life time of the material is further improved and enables a cost effective manufacturing of a pharmaceutical product for indications such as repair of the periodontal attachment apparatus.

A further aspect of the present invention is to provide a method for manufacturing the material of the above embodiments comprising
 (a) drying of the starting compounds,
 (b) milling and/or sieving of the water binding agent to reduce the particle size
 (c) and/or drying or burning of the water binding agent under conditions to obtain a water binding agent preferably a crystal water binding agent and to maintain the water binding capacity of the agent.

There are several advantages of the method of the present invention. Drying of the starting material already reduces the amount of free water in the material and thereby reduces the amount of a water binding agent necessary. In order to bind the residual water in the material the water binding agent is preferably a crystal water binding agent such as calcium sulfate, sodium sulfate and magnesium sulfate which will be transferred into a semihydrous and/or anhydrous chemical compound by drying or burning. In one aspect drying the water binding agent and other starting compounds of the biomaterial act synergistically. Furthermore, milling or sieving the water binding agent increases the specific surface of the component and, therefore, might further improve the water binding capacity of the water binding agent and inhibit or prevent polymer degradation.

Another embodiment of the present invention is a kit using the material above, the kit comprising a first receptacle to house at least one active agent and a second receptacle comprising the material of the invention. A separation of the active agent and the biomaterial surprisingly increased the shelf-life time of the kit and/or active agent.

Preferably the active agent is stabilized by one or more additives such as disaccharides like trehalose or sucrose e.g.

against degradation. Furthermore, the active agent within the kit is a lyophilizate of the active agent, preferably the lyophilizate of the active agent comprises a bulking agent to achieve a strong and elegant lyophilizate. More preferably the bulking agent is mannitol, preferably in combination with a disaccharide preferably trehalose in a ratio between about 1:1 and 4:1, which results in a mechanically stable lyophilizate with concomitant stabilization of the active agent.

More preferably the solid content of the additive and bulking agent such as trehalose and mannitol amounts 2.5% or more within the formulated bulk solution of the active agent before lyophilization preferably with a solid content between 2.5 wt % and 5 wt %.

Surprisingly the inventors have found that the resulting lyophilization is formstable, has the best structural integrity and improved properties for reconstitution of the active agent in the material such as the material of Example 3, which was reconstituted in the material of Example 2.

In a further embodiment of the present invention, the first receptacle of the kit is adopted, which means that the first receptacle contains a smaller internal receptacle which contains the active agent and whereas the inner receptacle has no corners or undercuts except the opening where it is closed with a stopper and whereas the inner receptacle is in average smaller within further distance to the opening. The advantage of such a receptacle is an easy mixture of the content of the first and second receptacle of the kit and enables almost complete uptake of the mixed material for administration of the material to an animal or human tissue.

In another embodiment of the present invention, the material of the present invention can for example be used for preventing, alleviating or treating symptoms or conditions of diseases or abnormal conditions of cartilage, bone, connective tissue including tendon and or ligament, periodontal tissue, neural tissue, skin, mucous membranes, endothelium and epithelium but are not limited thereto. The materials can be used for promotion of bone growth, cartilage growth, wound healing, ulcer treatment, burns, warts treatment, tumor treatment, regeneration of connective tissue and bone repair, craniofacial, skeletal or dental applications, reconstructive surgery, disc regeneration, treatment of osteoporosis, osteoarthritis, acquired congenital craniofacial, skeletal or dental abnormalities, ischemic or traumatic injury and degenerative disc disease.

In a further embodiment of the present invention, the material of any of the above embodiments or the kit can be used for the preparation of a pharmaceutical composition for treatment of cartilage and/or bone defects, critical size defects, full thickness defects, non-union fracture, periodontitis, peri-implantitis, sinus-floor augmentation, maxillo-facial intrabony defects preferably periodontitis, more preferably surgical, non-surgical or minimal invasive treatment of periodontitis preferably while preventing formation of ankylosis.

In another embodiment, the material of any of the above embodiments can be used for the preparation of a pharmaceutical composition for periodontal and/or guided tissue regeneration comprising the steps of applying the therapeutic composition to the periodontal treatment site by minimal invasive technique after at least partial cleaning of the receiving site.

In yet another embodiment, the material of any of the above embodiments can be used for the preparation of a pharmaceutical composition for periodontal and/or guided tissue regeneration comprising the steps of applying the therapeutic composition directly into the periodontal pocket of the periodontal treatment site by syringe.

Further embodiments of the present invention are the following:

Use of a water binding agent for inhibiting of water induced polymer degradation in a polymer comprising material, wherein the water binding agent is not removed prior to application of the material.

Use of a water binding agent for inducing blood clot stabilization in a polymer comprising material, wherein the water binding agent is not removed prior to application of the material.

Use of a water binding agent for increasing storage stability in a polymer comprising material, wherein the water binding agent is not removed prior to application of the material.

DETAILED DESCRIPTION OF THE INVENTION

Figure 1:
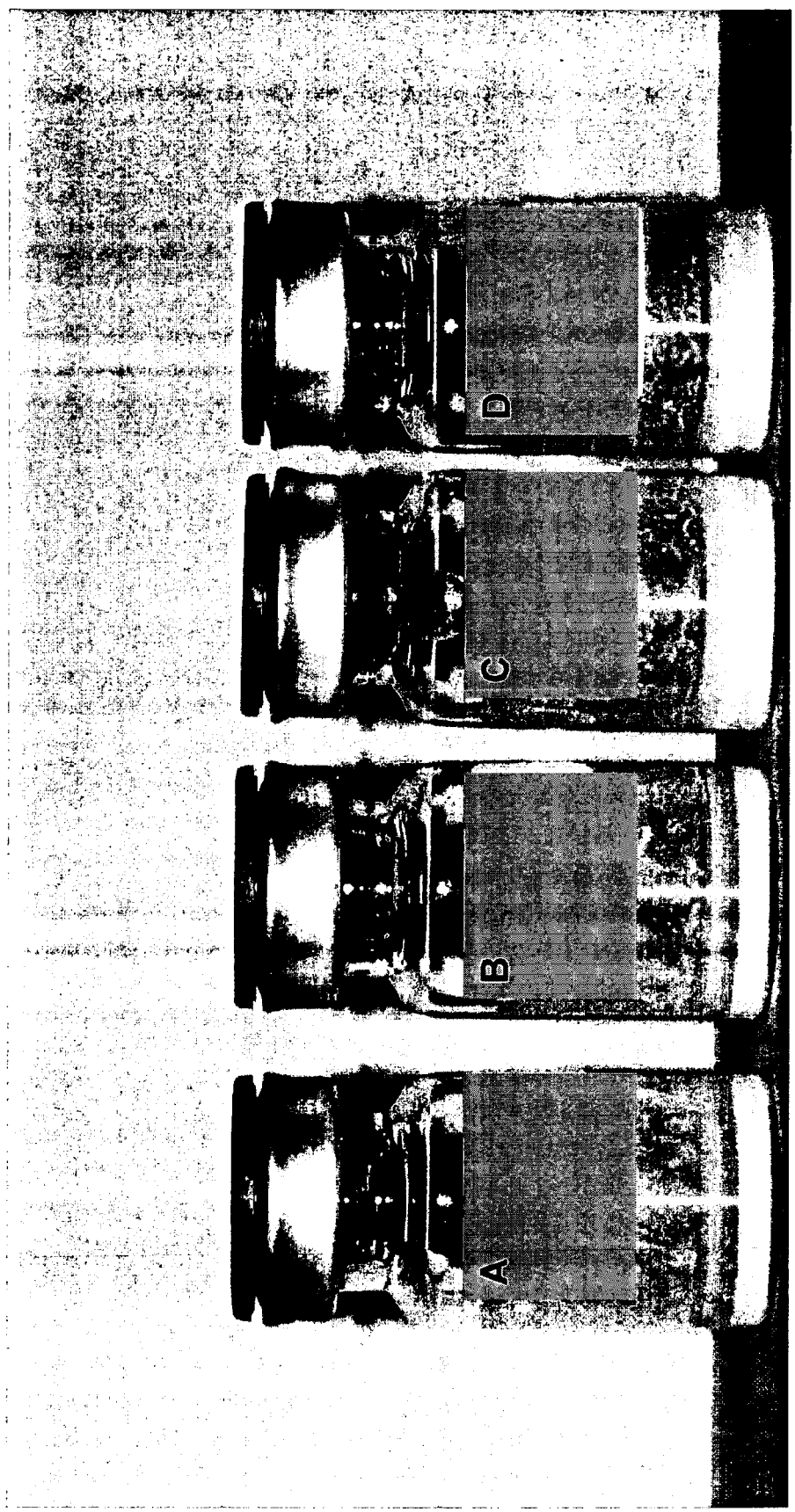
FIG. 1 illustrates the morphology of the different biomaterials after 4 weeks of storage in 6R-glass.

The term "water binding agent" means a substance which can physically adsorb and/or absorb or chemically adsorb water, therefore binding water molecules such as to prevent or inhibit degradation of the polymer.

Preferably, the water binding agent is a substance, which is able to bind free or unbound water, preferably to bind crystal water or to bind physically absorbed water into the structure, interior or cavity of the substance such as in the case of silicagel. The water binding agent can also be a substance, which is itself preferably degraded over the polymer by the free water in the material of the present invention or is able to react with water to protect water induced polymer degradation. Preferably, the degradation or reaction products of such a water binding agent are not aggressive reaction products, which might induce the degradation of the polymer. An example for such substance is magnesium ethanolate.

Preferably, the water binding agent or their water induced degradation product or products are not strong acid and/or strong basic chemical compounds. Preferably, the water binding agent is a non-toxic pharmaceutical acceptable solid or liquid and/or pH neutral intrinsic drying agent within the material of the present invention.

Preferably, the water binding agent is a chemical compound water free binding agent or a chemically combined water binding agent, more preferably the water binding agent is silicagel, zeolite, dewatered calcium sulfate dehydrate, calcium sulfate semihydrate, calcium sulfate anhydrous, sodium sulfate anhydrous, magnesium sulfate anhydrous, potassium carbonate, magnesium oxide anhydrous, magnesium ethanolate, calcium ethanolate, aluminium ethanolate and mixtures thereof. Most preferably the water binding agent is calcium sulfate semihydrate or anhydrous, preferably of less than 25 wt %, less than 20 wt %, between 4 wt % and 20 wt %, between 8 wt % and 15 wt %.

The term "water-free" means that the material contains less than 5 wt %, more preferably less than 3 wt %, even more preferably less than 2 wt %, most preferably less than 1 wt % water determined by methods such as the Karl Fischer method. Preferably, the term water-free means that only trace amounts of free-water (e.g unbound water) are detectable in the material, preferably less than 1 wt %, more preferably less than 0.5 wt %. The reduced amounts of free-water may decrease the degradation rate of the polymer such as for example the PLGA, thus increasing the shelf-life of the material.

The term "anhydrous" according to the present invention means a dewatered substance or substance with a reduced amount of crystal water bound, preferably with less than 2 mol water bound, less than 0.5 mol, more preferably about 0.18 to 0.5 mol water per mol substance which is still capable of binding free water or maintains the water binding capacity of the agent and which is capable of removing water from the surrounding (of external origin or bound to individual components of the polymer material) by chemical combination.

Preferably, the water binding agent has been milled, sieved and/or heat treated or any combination thereof. Preferably, the water binding agent of the above embodiments has a particle size of less than 150 µm, more preferably less 50 µm, most preferably of less than 20 µm.

The term "polymer" means a synthetic or natural polymer, more preferably a water sensitive or water degradable polymer, most preferably a water insoluble polymer, i.e. it does not form a homogeneous phase when admixed with water.

Preferably, the polymer is soluble or miscible in a plasticizer or organic solvent and capable of solidifying in an aqueous media or body fluid to form a solid or semi-solid implant upon removal of the plasticizer into the surrounding tissue. More preferably said water insoluble polymer is a "biocompatible", a "biodegradable" and/or a "bioresorbable" polymer.

Preferably, said polymer is selected from the group consisting of poly(alpha-hydroxy acids), poly (ortho esters), poly (anhydrides), poly(aminoacids), polyglycolid (PGA), poly-lactid (PLLA), poly(D,L-lactide) (PDLLA), poly(D,L-lactide-co-glycolide) or poly(L-lactide-co-glycolide) (PLGA), poly(lactic-co-glycolic acid) polyethylene glycol (PLGA-PEG) copolymers, poly(3-hydroxybutyricacid) (P(3-HB)), poly(3-hydroxy valeric acid) (P(3-HV)), poly(p-dioxanone) (PDS), poly(epsilon-caprolactone) (PCL), polyanhydride (PA), copolymers, terpolymers, blockcopolymers, combinations, mixtures thereof. Preferably the polymer is a synthetic polymer. In a more preferred embodiment, the synthetic polymer is a fast resorbable and/or biodegradable synthetic polymer, more preferably a polymer with a short chain length (20 to 40 monomer units of lactic acid or glycolic acid), most preferably a polymer which comprises 20 to 40 monomer units of lactic, preferably a non-endcapped PLGA with a lactic-/glycolic acid ratio of 50:50 and an inherent viscosity between 0.16-0.24 dl/g (related to a 0.1% wt solution of the respective polymer in chloroform at 25° C.).

In another embodiment of the present invention the water insoluble polymer is a PLGA-PEG copolymer, preferably a PLGA-PEG diblock- or triblock-copolymer.

The term "polymer comprising material" means a material, preferably a biomaterial, which is composed of at least one polymer, more preferably composed of two pharmaceutical accepted substances, most preferably a multi-component system, whereas one substance is a biodegradable and/or bioresorbable polymer intended for parenteral or topical application. Preferably the material is a semi-solid or liquid material.

The material according to the invention includes a device, an implant, a tissue regeneration material, an injectable and/or moldable biomaterial or implant, a bone filler and bone replacement material such as tri-calcium phosphate and hydroxyapatite, a screw, a drug delivery systems, a hydrogel, an in situ hardening implant, a porous implant or tissue regenerating material, a pharmaceutical composition or product, an osteoinductive material, a periodontal regeneration material, a connective tissue regeneration material and an alveolar bone, cementum and/or periodontal ligament regeneration material. The material according to the invention is preferably a biomaterial.

Preferably, the material is a polymer liquid such as but not limited to a polymer solution, a suspension or a dispersion, where for example the polymer is dissolved in an organic solvent or plasticizer such as polyethylene glycol or N-methyl-pyrrolidone.

More preferably, the polymer comprising material forms a macroporous matrix after in situ hardening of the material, wherein the polymer comprising material preferably contains a substance, matrix, polymer and/or active agent which has thrombogenic, blood clot inducing and/or hemostatic activity.

This material has the advantage to for example adhere more to the tissue defect and therefore improve tissue regeneration.

The term "geometry" refers to the fact that the outer boundary of the material of the present invention is not significantly changed and more or less maintained after in situ hardening compared to the material before in situ hardening e.g. it does not alter the form of a rounded shaped formulation within a syringe into a flattened film-like appearance after in situ hardening. However, the porosity of the material does change upon in situ hardening e.g a porous scaffold is formed or the material might swell due to a swelling agent encompassed.

The term "plasticizer, first plasticizer or organic solvent" according to the present invention means a water soluble or water miscible organic liquid or solvent which is pharmaceutically acceptable or a mixture thereof. The function of the plasticizer is for example to dissolve the water insoluble biodegradable, biocompatible and/or bioresorbable polymer.

The term "dissolving" means the dissolution or suspension of a substance in a liquid, yields to a homogenous distribution of the substance within the liquid.

Preferably said plasticizer is biocompatible. More preferably, said plasticizer is selected from the group consisting of polyethylene glycol (PEG) 400, PEG 200, PEG 300, PEG 600, polypropylene glycol, 1,3 butandiole, castor oil, C2 to C6 alkanols, propylene glycol, solketal, acetone, methyl acetate, ethyl acetate, ethyl lactate, methyl ethyl ketone, dimethylformamide, dimethyl sulfoxide, dimethyl sulfone, tetrahydrofuran, decylmethylsulfoxide, oleic acid, propylene carbonate, N,N-diethyl-m-toluamide, 1-dodecylazacycloheptan-2-one or mixtures thereof. Most preferably, said plasticizer is polyethylene glycol, preferably selected from the group consisting of polyethylene glycol (PEG) 400, PEG 200, PEG 300.

The term "biodegradable" specifies materials for example polymers, which break down due to macromolecular degradation with dispersion in vivo but for which not necessarily the proof exists for the elimination from the body. The decrease in mass of the biodegradable material within the body is the result of a passive process, which is catalyzed by the physicochemical conditions (e.g. humidity, pH value) within the host tissue.

The term "bioresorbable" specifies materials such as polymeric materials, which undergo degradation and further resorption in vivo over time; i.e. polymers, which are eliminated through natural pathways either because of simple filtration of degradation by-products or after their metabolisation. Bioresorption is thus a concept, which reflects total elimination of the initial foreign material. In a preferred embodiment said bioresorbable polymer is a polymer that undergoes a chain cleavage due to macromolecular degradation in an aqueous environment. It has to be mentioned that the term "resorption" always describes an active process.

The term "polymer degradation" means a decrease in the molecular weight of the respective polymer. With respect to the polymers, which are preferably used within the scope of the present invention said degradation is induced by free water due to the cleavage of ester bonds. The degradation of the polymers as for example used in the biomaterial as described in the examples follows the principle of bulk erosion. Thereby a continuous decrease in molecular weight precedes a highly pronounced mass loss. Said mass loss is attributed to the solubility of the degradation products. Methods for determination of water induced polymer degradation are well known in the art such as titration of the degradation products, viscometry, differential scanning calorimetry (DSC) and those described in Example 5.

Moreover, the material further comprises additional additives or excipients such as an inorganic filler, an organic filler, a pore forming agent, a pore initiating filler, an alcohol, a sugar or at least a second polymer or any combination thereof to modulate the characteristics of the biomaterial (e.g. appearance, degradation time, porosity, stability). Preferable, the biomaterial is a biodegradable and/or bioresorbable biomaterial. Preferably, the polymer comprising material is suitable for tissue replacement or preferably transient tissue replacement.

The term "inorganic filler" means a compound insoluble or poorly soluble in water, i.e. which does not form a homogeneous phase when admixed with water. Said inorganic filler can serve different functions such as structuring of the matrix or scaffold within a polymer based material, improvement of osteoconductive properties and/or the mechanical performance of the material, serving as a scaffold for cell ingrowth, regulating degradation of the material for example to guide tissue regeneration and replacement of the material by newly formed tissue, enabling blood clot stabilization, reducing the polymer content in the material preferably without alteration of the mechanical properties of the material, serving as a carrier for an active agent and/or modification of the release of an active agent.

Preferably said inorganic filler is an inorganic compound.

Preferably, the inorganic compound is selected from the group of magnesiumoxide, magnesiumhydroxide, magnesium carbonate, silicium dioxide or a calcium compound. More preferably, the inorganic compound is a calcium phosphate, calcium sulfate or calcium carbonate, most preferably tricalcium phosphate, beta-tricalcium phosphate ($\beta$-TCP), alpha-tricalcium phosphate ($\alpha$-TCP), apatite, calcium phosphate containing cement or tetracalcium phosphate, or a mixture of the above various different inorganic, preferably calcium containing compounds. Most preferably the inorganic filler is calcium sulfate.

The term "organic filler" includes substances that can be added to increase bioadhesion of the material or implant for example collagen. Such components can further affect the final mechanical properties (e.g., tensile strength, torsion) of the implant comparable to the function of collagen within natural bone such as fiber reinforcement. Preferably the organic compound is selected from chitosan, collagen, calcium alginate, poly(2-hydroxyethyl methacrylate), hyaluronic acid or derivatives thereof, cellulose or derivatives thereof, or starch or derivatives and/or any combinations thereof.

The term "pore forming agent" means a compound which, when added to the material increases the number and size of micro- and macropores within the in situ formed implant ex vivo or in the organism. Included but not limited to are those substances which when in contact with aqueous media increase their volume and dissolute into the surrounding fluid leaving behind a porous preferably interconnected structure. Other pore forming agents are substances, which introduce a porosity by dissolution into aqueous media analogous to sodium chloride (salt leeching effect) or which will provide pores when dissolved. In addition, these compounds might also stabilize the forming porous structure of the material.

Pore forming agents of the present invention include pharmaceutical acceptable compounds which dissipate from the in situ formed implant and thereby result in pore formation within the implant.

In one embodiment the pore forming agent is a swelling agents. Other swelling agents according to the present invention are blasting agent's known to experts in the field from manufacturing of tablets.

Pore forming agents of the present invention also include compounds such as sodium alginate, amylase, amylopectine, starch, hyaluronic acid, sodium hyaluronate, gelatine, collagen, carboxymethylcellulose, methylcellulose, carboxymethylcellulose calcium salt, carboxymethylcellulose calcium salt, hydroxylprorpyl methylcellulose, hydroxybutylmethylcellulose, hydroxyethylcellulose, hydroxyethylcellulose, or methylhydroxyethylcellulose, surfactants, preferably block copolymers of ethylene oxide/sorbitan and propylene oxide such as Pluronics® or Tween® 80 (e.g., Polysorbate 80; Montanox® 80; Polyoxyethylene sorbitan monooleate). Included are also porogenic substances such as sugars or salts of crystal size, which will provide pores when dissolved in the implant in situ and/or agents which form $CO_2$ gas bubbles and thereby leaving pores when moved from the implant.

The term "polymer reinforced matrix or scaffold" means a material wherein the polymer functions as a binding agent or immobilization agent for another component or components of the material such as a bone or tissue replacement material, an inorganic filler, a calcium phosphate or hydroxyapatite to form a matrix or scaffold for ingrowth of cells and/or tissue regeneration.

The term "space providing" means a scaffold which is able to provide a space for blood clot stabilization and/or tissue regeneration which preferably almost degrades within several weeks or month, more preferably almost degrades within four weeks and most preferably has already been degraded to a significant percentage preferably more than 60%, 70%, 80%, 85%, 90% within two weeks and does not interfere or obstruct with the newly formed tissue. It also means space maintenance even when additional materials such as absorbable membranes are used because it will prevent it from collapsing.

The term "reinforced hydrogel" means a hydrogel mechanically stabilized by a polymeric matrix, which functions for example as a blood clot substitute.

The term "in situ hardening implant" as used in the present invention refers to a solid or semi solid implant being formed after contact of the polymer comprising material of the present invention with an aqueous medium such as water, a physiological solution or body fluid after dissipation or dissolution of an organic solvent or plasticizer into the surrounding ex vivo as well as in an organism such as a human or an animal body or tissue.

During the preferred in situ hardening in contact with aqueous medium or body fluid the plasticizer diffuses out of the material such as those liquid or moldable materials as described in the examples of the present invention, leaving pores and leading to a solid or semi-solid biomaterial, composite device or in situ implant. Therefore, the plasticizer might be a water soluble or water miscible solvent, or is a liquid, preferably a water soluble or miscible polymer. Preferably the plasticizer has a low impact on the glass transition temperature of the water insoluble polymer in the in situ hardened implant and if necessary is compatible with the active agent. Dependent on the water insoluble polymer a plasticizer selected from a group of plasticizers further defined above should be used with the lowest impact on the glass transition temperature of the polymer after setting. It is also encompassed that upon diffusion of the plasticizer out of the material other substances or particles such as matrix stabilization agents or microparticles are embedded in the polymer comprising material forming a porous matrix or scaffold for cell ingrowth and/or tissue regeneration or delivery of drugs and/or active agents into the surrounding tissue.

The term "blood clot stabilization or stabilized blood clot" means a feature of a biomaterial to fix an in vivo or in vitro formed blood clot within the material to form a matrix or network in which substances like those contained in the blood clot and preferably blood cells are entrapped such that the blood clot is not only localized on the outer surface of the biomaterial but also within the interior of the matrix, preferably distributed all over the matrix of the formed biomaterial.

The term "active agent" comprises a protein, polypeptide or a small molecule drug, an antibiotic, anti-infective, antiviral, antimicrobial, antiinflammatory, wound healing, cytostatic, cytotoxic, anesthetic, a growth factor, a morphogenetic protein, a bone morphogenetic protein such as proteins of the TGF-β superfamily including BMPs and GDFs (e.g. BMP-1, BMP-2, BMP-3, BMP-4, BMP-5, BMP-6, BMP-7, BMP-8, BMP-9, BMP-10, BMP-11, BMP-12, BMP-13, BMP-14, BMP-15 and BMP-16, GDF-1, GDF-2, GDF-3, GDF-4, GDF-5, GDF-6, GDF-7, GDF-8, GDF-9, GDF-10 and GDF-11), fibroblast growth factors, transforming growth factor β, keratinocyte growth factor, nerve growth factor, or proteins of the extracellular matrix selected such as fibronectin, laminin, collagen, or proteins involved in the clotting cascade, a periodontal ligament, cementum and/or alveolar bone inducing agent or biological active fragments or variants thereof. Preferably, the active agent is a periodontal ligament, cementum and/or alveolar bone inducing agent. More preferably, the active agent is selected from the group of GDF-5, BMP-2 and BMP-7.

The term "periodontal regeneration" comprises procedures which are specifically designed to restore parts of the tooth-supporting apparatus which have been lost due to periodontitis (Lindhe, J., Lang, N. P. & Karring, K. (2003) Periodontology and Implant Dentistry. 4th edition, Oxford. Blackwell Munksgaard, Chapter 28 page 651). Regeneration is defined as a reproduction or reconstruction of a lost or injured part in such way that the architecture and function of the lost or injured tissues are completely restored. Several methods are known for experts in the field to treat periodontitis. Treatment of moderate periodontitis can be achieved by non-surgical therapy, whereas in more advanced cases (e.g., in the presence of intrabony defects or furcations) the treatment procedure will be supplemented with periodontal surgery. Several techniques are known in periodontal pocket surgery (e.g flap procedures), which are described in Lindhe, J., Lang, N. P. & Karring, K. (2003) Periodontology and Implant Dentistry. 4th edition, Oxford. Blackwell Munksgaard, Chapter 25, page 522-534.

The term "guided tissue regeneration" involves the placement of a physical barrier (e.g., e-PTFE or collagen membranes) to ensure that the periodontitis-affected root surface becomes repopulated with cells from the periodontal ligament. Examples of barrier materials for regenerative surgery are described for example in Lindhe, J., Lang, N. P. & Karring, K. (2003) Periodontology and Implant Dentistry. 4th edition, Oxford. Blackwell Munksgaard, Chapter 28.

To improve the periodontal regeneration at least partial cleaning of the receiving site of the material of the present invention will be performed.

The term "cleaning" means cleaning or decontamination of the receiving site e.g. tissue site of contaminated material such as granulation tissue as for example used for the treatment of periodontitis by using instruments such as curettes, drills or bone rongeurs. Methods and instrumentation for cleaning the receiving site are described in more detail for example in Lindhe, J., Lang, N. P. & Karring, K. (2003) Periodontology and Implant Dentistry. 4th edition, Oxford. Blackwell Munksgaard, Chapter 20, page 432-441, Chapter 25, page 540-549).

The term "receiving site" means the area where the material will be placed for treatment of periodontal defects e.g. periodontitis.

For a preferred use of the material of the present invention for preparation of a pharmaceutical composition for periodontal and/or guided tissue regeneration the therapeutic composition is directly applied into the periodontal pocket of the periodontal treatment site by syringe. This avoids painful surgery for the patient.

DESCRIPTION OF THE FIGURES

Figure 2:
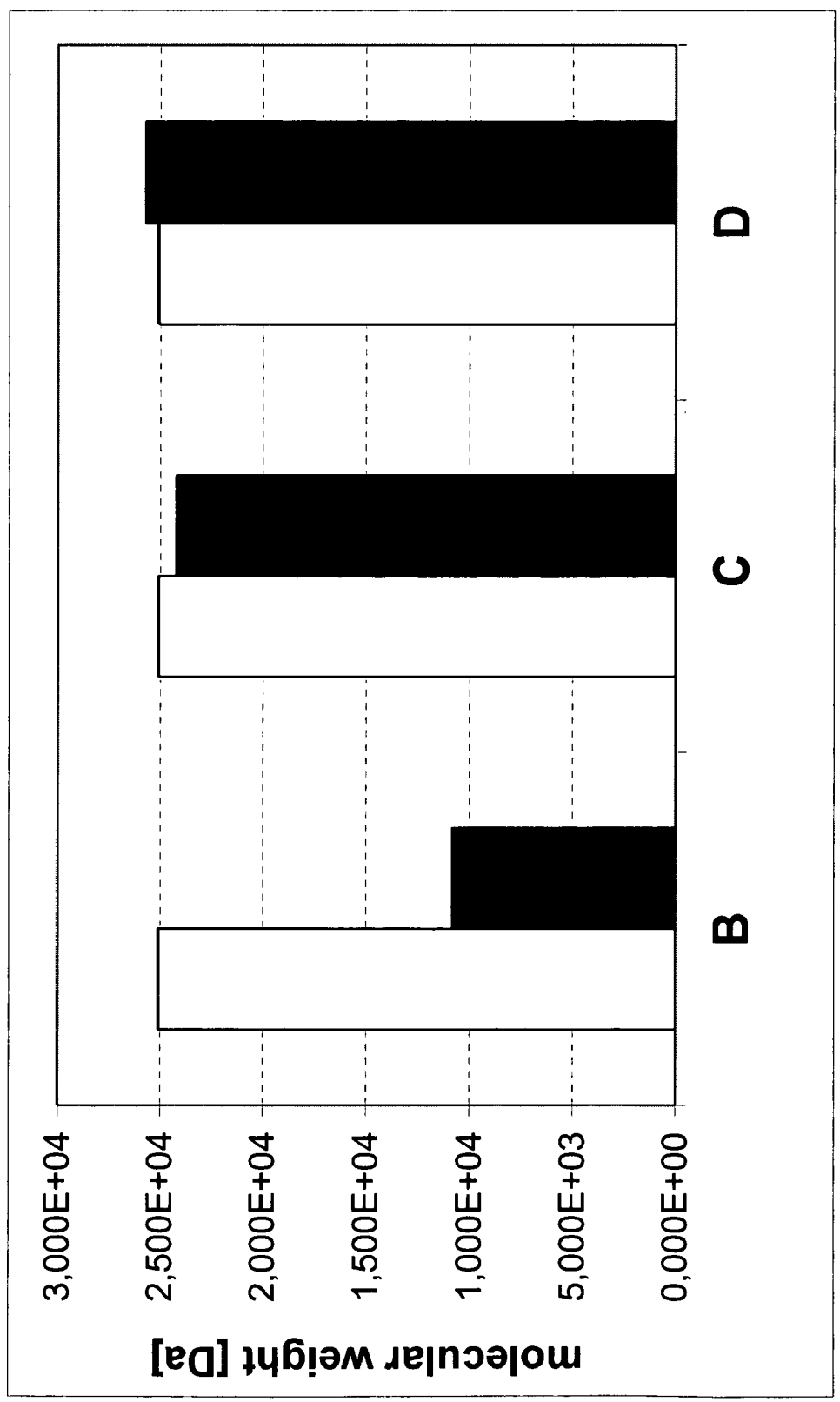
FIG. 2 illustrates the degradation of the poly-(lactic-co-glycolic-acid) composition after 4 weeks compared to the freshly prepared biomaterial dependent on the content of the water binding agent.
Figure 3:
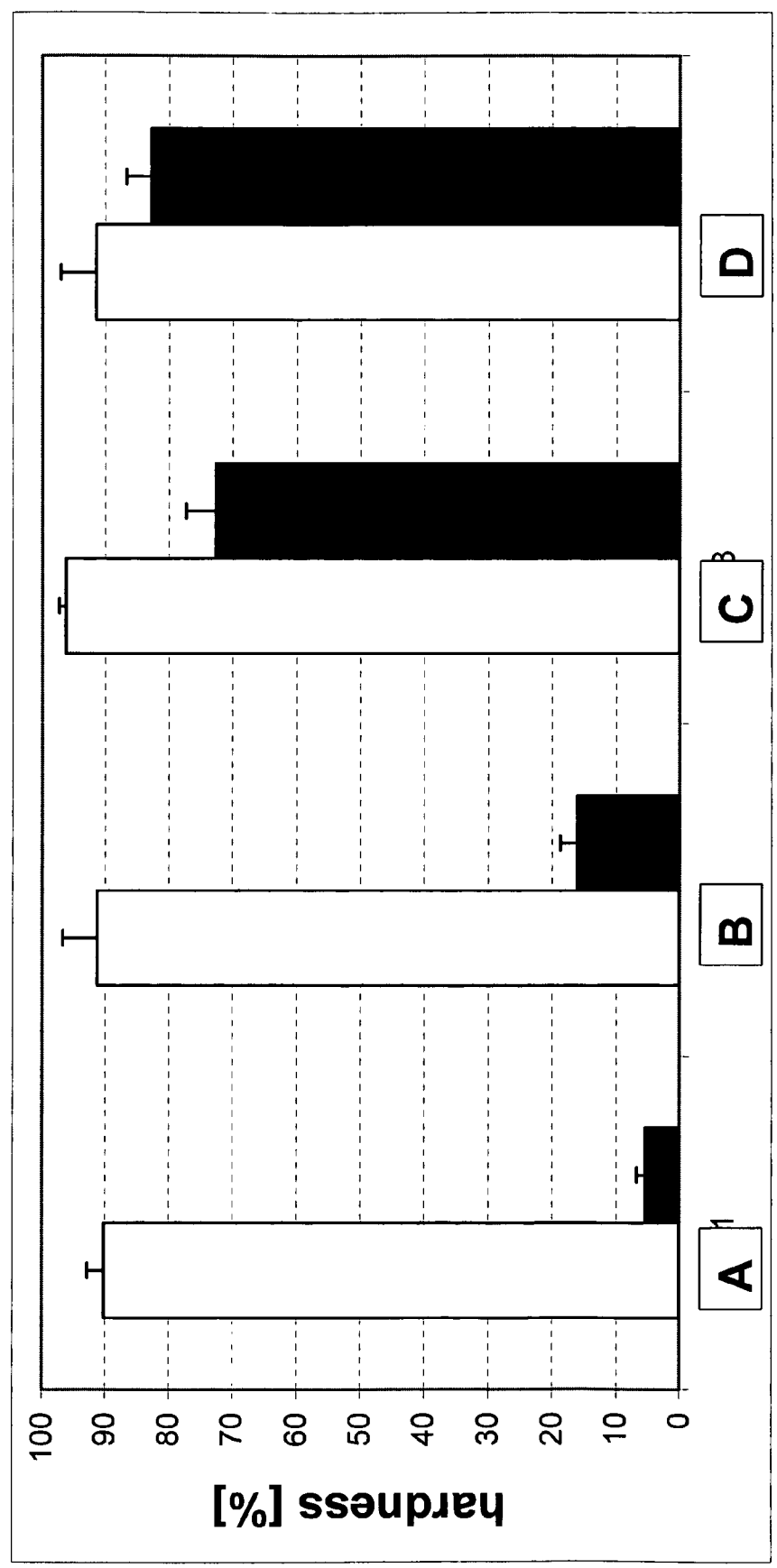
FIG. 3 illustrates a comparison of the mechanical stability of the poly-(lactic-co-glycolic-acid) composition after 4 weeks compared to the freshly prepared biomaterial dependent on the content of the water binding agent.
Figure 4:
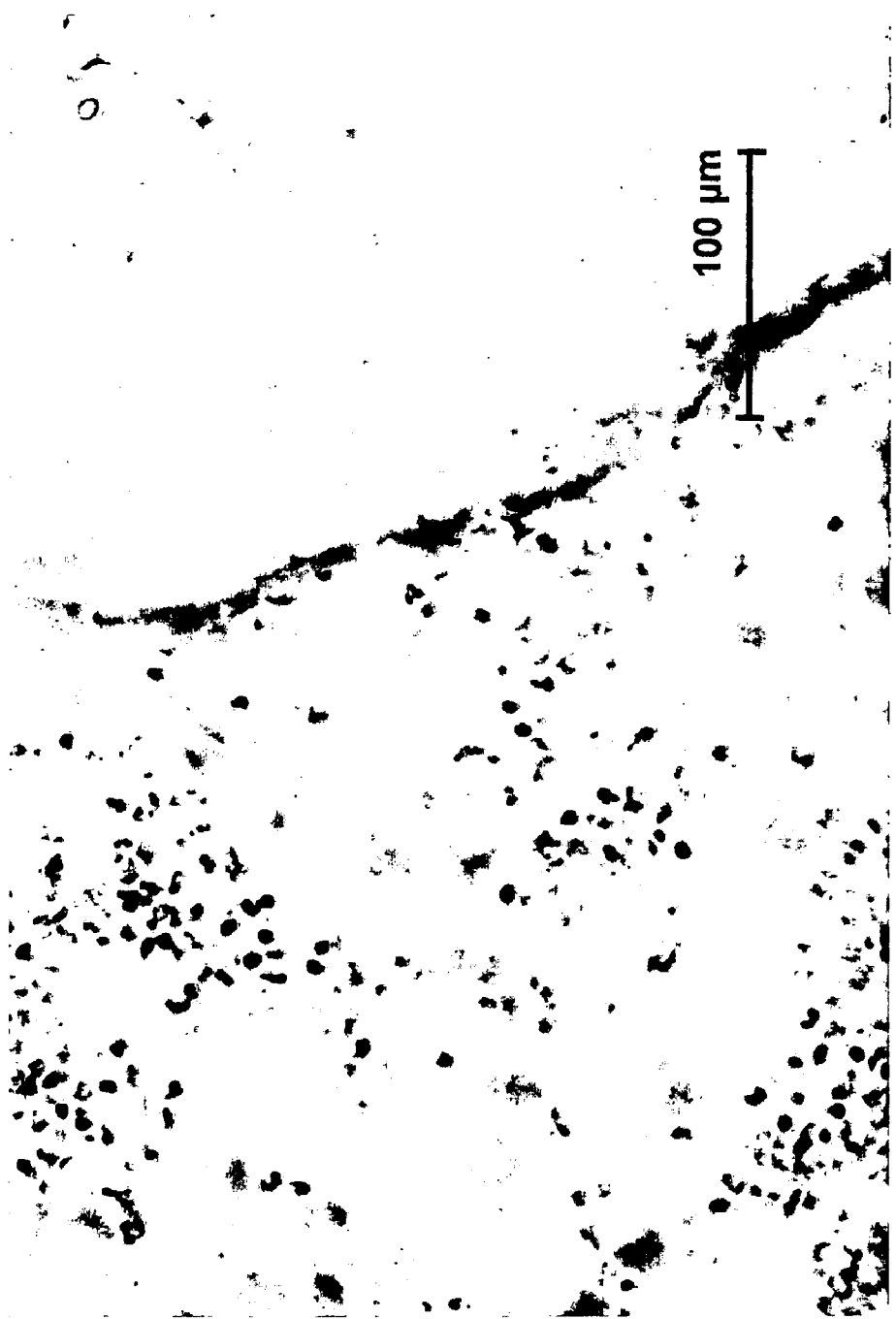
FIG. 4 illustrates the blood clot inducing activity of the biomaterial in the outer layer of the biomaterial.
Figure 5:
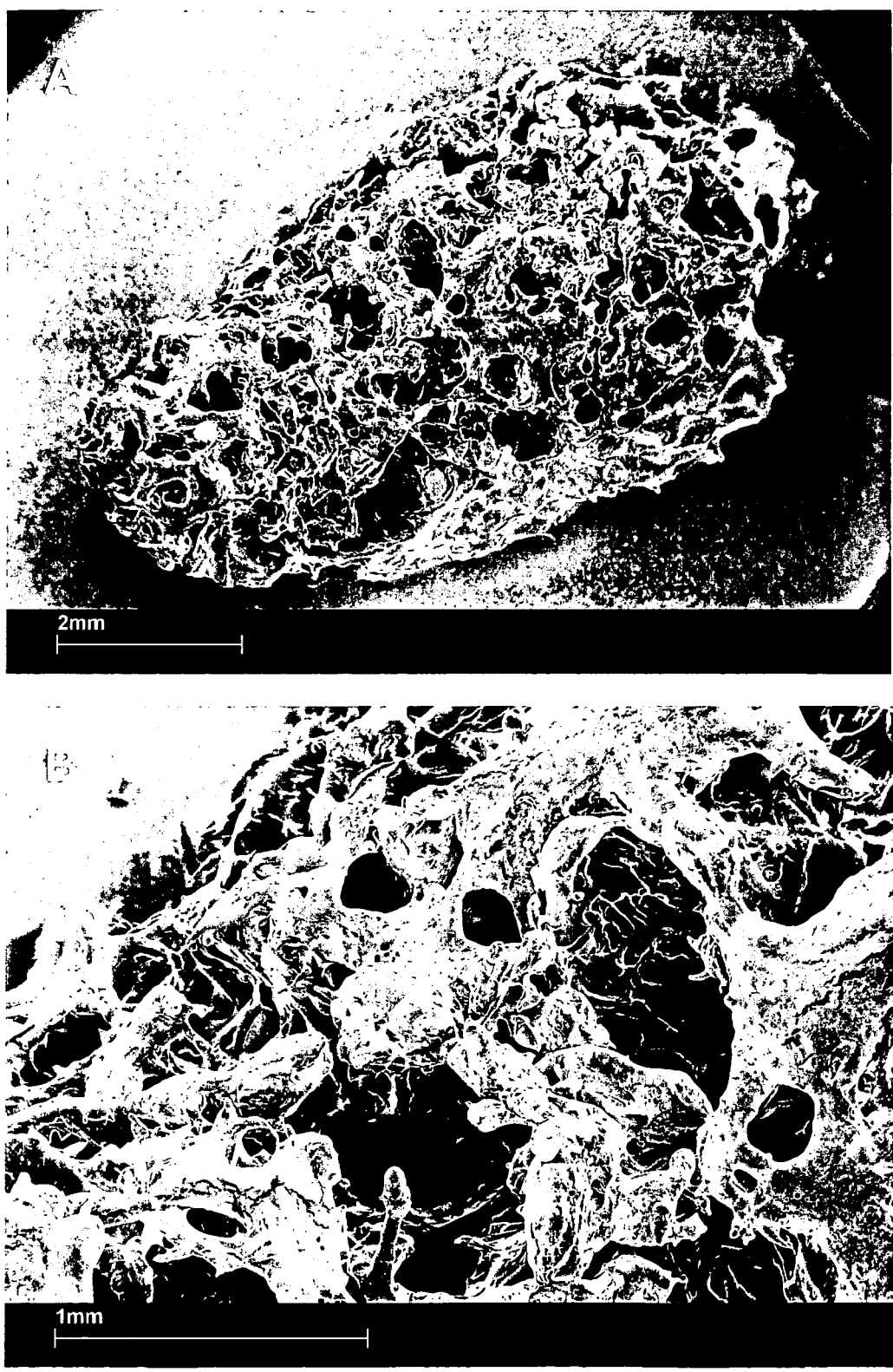
FIG. 5 illustrates the sponge-like overall porous appearance of the biomaterial after in situ hardening.

Detailed aspects of the present invention are described in the following by reference to FIGS. 1-6. FIGS. 1-3 are based on formulations prepared according to Example 1, FIGS. 4 and 5 are based on formulations prepared according to Example 2, FIG. 6 on the formulation of Example 12.

FIG. 1 shows preparations of the biomaterial after 4 weeks of storage in 6R-glass vials at 37° C. As FIG. 1 reveals formulations A and B exhibited a highly pronounced phase separation due to sedimentation of the inorganic filler used in these samples, which is attributed to the polymer degradation. According to Stokes's law describing the sedimentation rate of spherical particles by the following equation $$F = 6 * \pi * r * \eta * v$$

where F is the frictional force, r the radius of the particles, η the dynamic viscosity of the fluid and v the sedimentation rate, a decrease in viscosity of the fluid yield an increased sedimentation rate. As the particle size of the inorganic filler has remained constant during storage the observed sedimentation of said component can be attributed to a reduced viscosity of the polymer solution. Said decrease in viscosity of the polymer solution has to be due to a cleavage of ester bonds within the poly(lactic-co-glycolic-acid) molecules in the presence of water. Since formulation C and D containing higher amounts of calcium sulphate anhydrous, which acts as an internal drying agent, these formulations exhibited no visible phase separation.

FIG. 2 illustrates a comparison of the molecular weight of the material, determined according to Example 5 of the isolated poly-(lactic-co-glycolic-acid) after 4 weeks of storage (dark column) with its initial molecular weight without storage (bright column). These data indicate that increasing amounts of calcium sulphate anhydrous are able to suppress the hydrolytic degradation of the polymer, which is due to its water binding capacity by transferring free water within the formulation into non-reactive crystal water. Thereby a content of about 4 wt % (formulation B) of calcium sulphate anhydrous was able to substantially weaken the decrease in molecular weight of the polymer during storage. About 8 to 12 wt % (formulation C and D) of calcium sulphate anhydrous nearly fully inhibited polymer degradation.

FIG. 3 shows a comparison of the mechanical stability determined according to Example 6 of the biomaterial immediately after manufacturing (bright column) and after 4 weeks of storage (dark column). Since the mechanical stability of the biomaterial mainly depends on the molecular weight of the polymer used, this parameter is suitable to detect polymer degradation. FIG. 3 revealed a distinct decrease in mechanical stability for Formulations A, and B, which is less pronounced for increasing contents of calcium sulphate anhydrous. This has to be attributed to its water binding capacity, leading to a reduction of free water within the respective formulations. Therefore the cleavage of ester bonds within the poly(lactic-co-glycolic-acid) could surprisingly minimized.

FIG. 4 shows the histology at the interface between the surrounding blood clot and the biomaterial (LM-micrograph, hematoxylin staining of a cryo-section following ethanol fixation, magnification 200×) after in situ hardening of the biomaterial of the present invention in human whole blood at 37° C. for 12 hours according to Example 10.

One advantage of the present invention is that the biomaterial is able to interact with the naturally arising blood clot such as for example within a bleeding tissue site not restricted to a periodontal defect site, leading to an intimate binding between the natural tissue and the synthetic biomaterial, thus resulting in an accelerated on-site stability of the porous space providing scaffold within the defect site of the patient.

FIG. 5 shows the outer and inner porosity of the biomaterial according to Example 10 mixed with the drug lyophilizate of Example 3 as described under Example 4 after in situ hardening in an aqueous medium at 37° C. and upon drying. Image A shows the in situ hardened sponge-like outer surface of the biomaterial exhibiting pores distributed onto the sponge-like outer surface.

Image B shows an enlargement of the inner part of the biomaterial, exhibiting pores with an average diameter of approximately 500 µm, which is a basic requirement for integration of the implant material within the surrounding tissue and cell migration from the surrounding tissue into the space-providing matrix.

Figure 6:
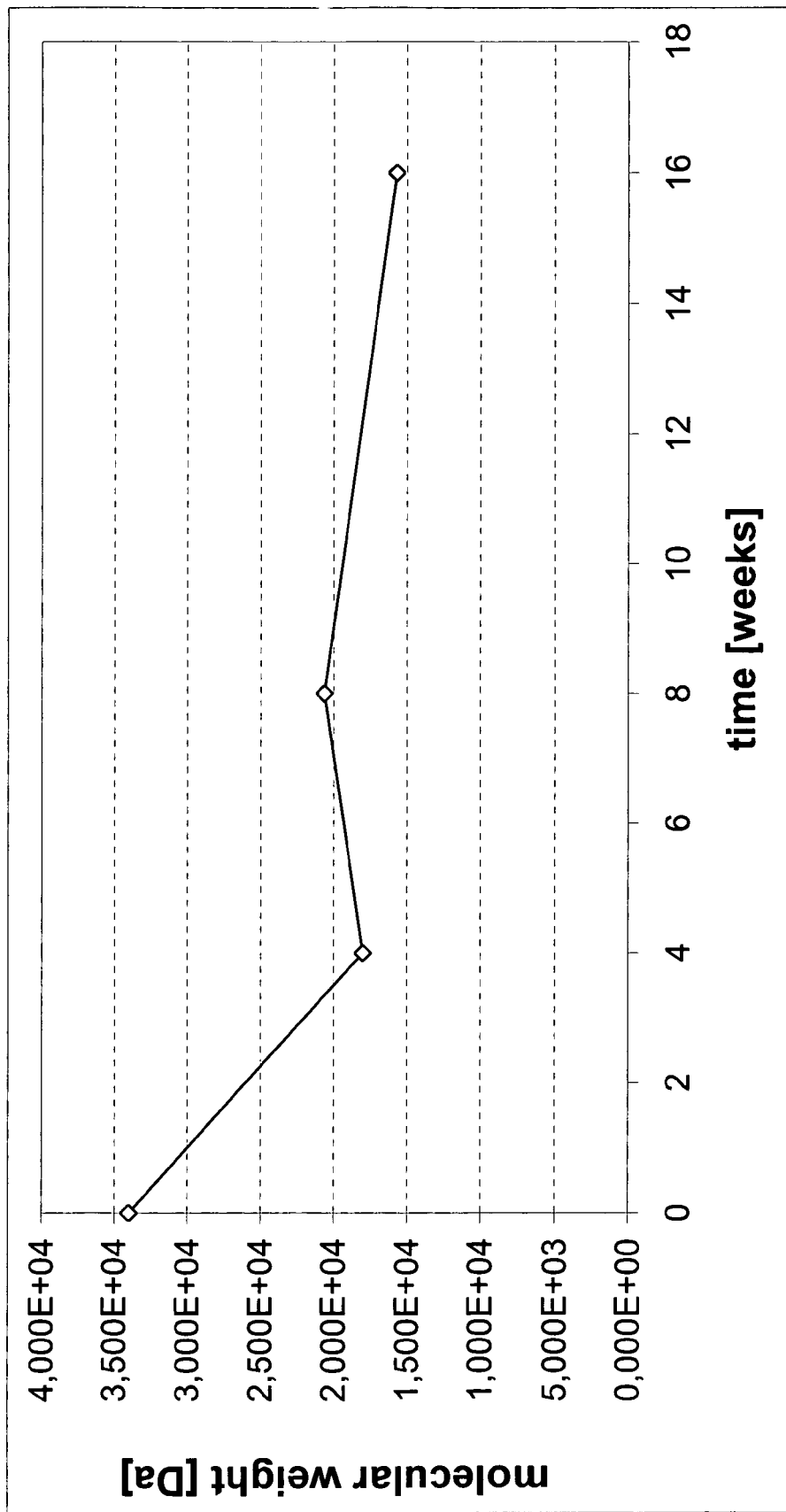
FIG. 6 illustrates the decrease in molecular weight over time of a PLGA dissolved in PEG 400.

FIG. 6 displays the decrease in molecular weight of the polymer component within the formulation manufactured according to Example 12 during storage at 4° C. and a relative humidity of 50% in a 6R-glass vial. This Fig. reveals that the molecular weight of the polymer used, as determined according to Example 5, was about 50% reduced after 4 weeks of storage compared to the molecular weight of the polymer after manufacturing which can be overcome by addition of the water binding agent according to the present invention.

Figure 7:
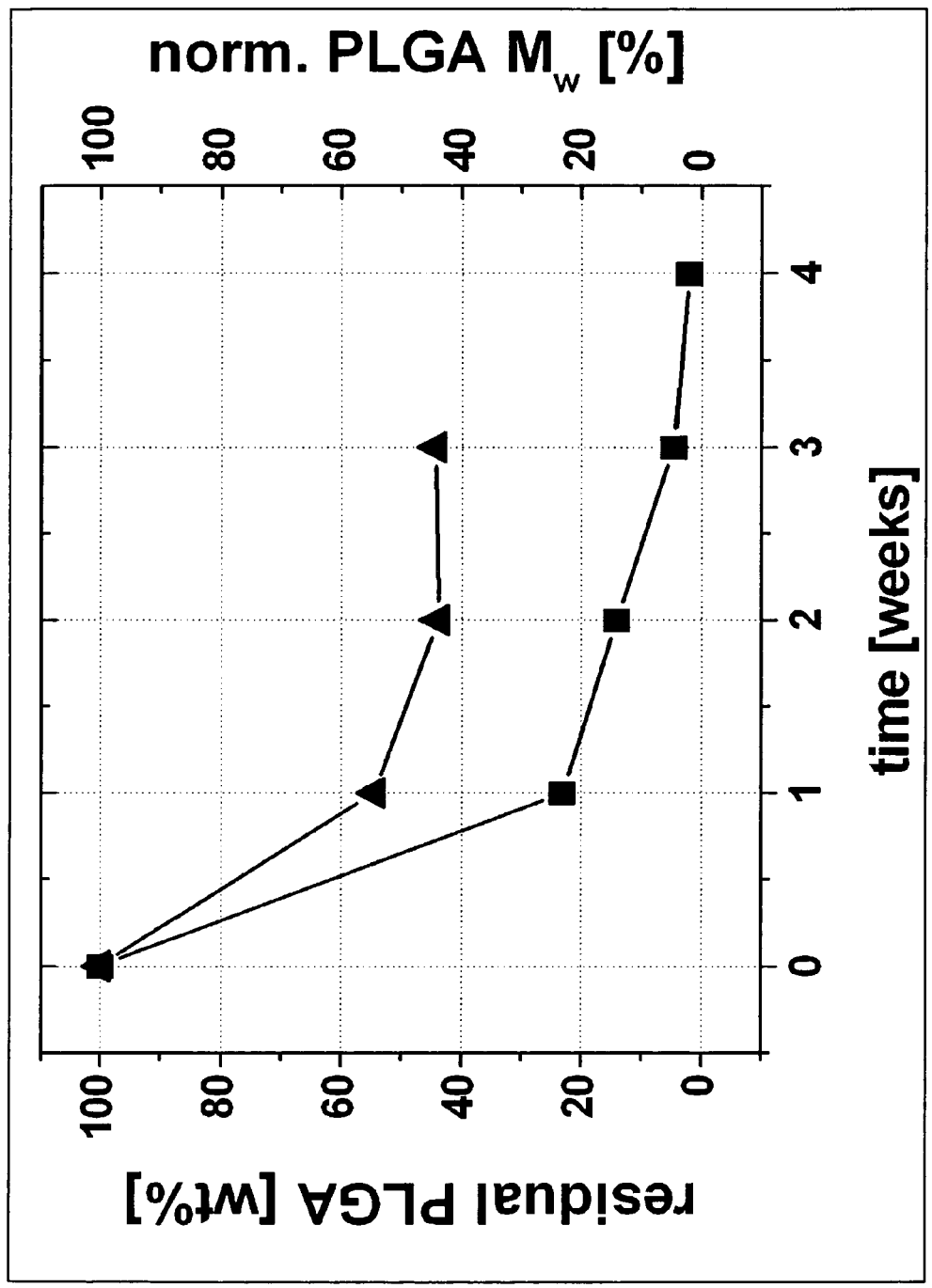
FIG. 7 illustrates the normalized decrease in residual PLGA mass and the normalized decrease in PLGA molecular weight of the biomaterial during in-vitro degradation studies over 4 weeks in PBS at 37° C.

FIG. 7 shows the normalized decrease in residual PLGA mass (square symbols; analyzed by weight balance) and the normalized decrease in PLGA molecular weight (triangular symbols, analyzed by GPC-MALLS) as the polymer component within the formulation manufactured according to Example 2 during in-vitro degradation studies over 4 weeks in PBS at 37° C.

DETAILED DESCRIPTION OF THE PREFERRED EMBODIMENTS

The present invention provides the following embodiments:

1. A polymer comprising material comprising a water binding agent, wherein the water binding agent is present in an amount sufficient to physically or chemically absorb water to prevent degradation of the polymer.

The water binding agent prevents water (i.e. external water or water introduced by the individual components of the polymer comprising material) from diffusion into the material and/or from degrading the polymer material by hydrolysis.

Preferred water binding agents are calcium sulphate anhydrous, sodium sulfate anhydrous, magnesium ethanolate or zeolithe.

Due to the presence of the water binding agent a "water-free" material is obtained.

The polymer material thus obtained shows a storage stability of more than one, three, six or twelve months.

2. The polymer comprising material of embodiment 1, wherein the polymer is a biodegradable and/or bioresorbable polymer, wherein more preferably the biomaterial is a polymer liquid or a polymer solution.

Polymer liquids or solutions are preferably injectable, more preferably injectable through a needle.

3. The polymer comprising material of embodiment 1 or 2, wherein the material is a biomaterial, preferably a pharmaceutical formulation.

4. The polymer comprising material of any of embodiments 1 to 3, wherein the material comprises a plasticizer, a pharmaceutical acceptable plasticizer or organic solvent.

After application into an aqueous liquid or body fluid the biomaterial preferably forms an in situ hardening implant.

5. The polymer comprising material of embodiments 4, wherein the plasticizer is polyethylenglycol or NMP, preferably in an amount of less than 55%, more preferably less than 50 wt % of the organic solution.

6. The polymer comprising material of any of embodiments 1 to 5, which comprises an inorganic filler, a pore forming agent, a pore initiating filler or at least a second polymer or any combination thereof.

Preferred biomaterials of such multi-component systems as of embodiment 6 are as set forth in WO 05/120595, except that said water binding agent or pore initiating filler is added.

After application into an aqueous liquid or body fluid preferred biomaterials form a polymer reinforced matrix or scaffold preferably a reinforced hydrogel and/or stabilized blood clot. Preferably the water binding agent in this embodiment is a $Ca^{2+}$ comprising water binding agent.

Preferred biomaterials of such multi-component systems form a sponge-like material in vitro or in vivo preferably with space providing properties. Preferably, the pore initiating filler is an organic water soluble substance, more preferably an alcohol, most preferably mannitol.

Preferably, the sponge-like material has a porosity of 40 vol % or more, 30 to 40 vol %, 60 to 80 vol %, more preferably a porosity of 50 vol % or more after in situ hardening.

7. The polymer comprising material of any of embodiments 1 to 6, which is a synthetic biodegradable and/or bioresorbable tissue regenerating biomaterial comprising a) at least one biodegradable and/or bioresorbable water insoluble polymer, preferably a fast resorbable and/or biodegradable polymer, more preferably a polymer with a short chain length, even more preferably of 20 to 40 monomer units, even more preferably a polymer which comprises 20 to 40 monomer units of lactic acid or glycolic acid, most preferably a polymer comprising a second polymer which is preferably not a natural polymer, b) optional a pore forming agent, preferably of less than 5 wt %, c) a pharmaceutical acceptable organic solvent, preferably polyethylenglycol, more preferably of an amount of less than 55%, more preferably less than 50% of the organic solution.

8. The polymer comprising material of any of embodiments 1 to 6, which is a synthetic biodegradable and/or bioresorbable tissue regenerating biomaterial comprising a) at least one biodegradable and/or bioresorbable water insoluble polymer, preferably a fast resorbable and/or biodegradable polymer, more preferably a polymer with a short chain length, even more preferably of 20 to 40 monomer units, even more preferably a polymer which comprises 20 to 40 monomer units of lactic acid or glycolic acid, most preferably a polymer comprising a second polymer which is preferably not a natural polymer, b) a pore forming agent, preferably of less than 5 wt %, c) an inorganic filler preferably an inorganic water insoluble filler, more preferably an inorganic water insoluble filler, which is not a calcium phosphate, most preferably an inorganic water insoluble filler which is calcium sulfate, d) optional a pore initiating filler, preferably an organic water soluble substance preferably an alcohol such as mannitol, e) a pharmaceutical acceptable organic solvent, preferably polyethylenglycol, more preferably of an amount of less than 55%, more preferably less than 50 wt % of the organic solution.

9. The polymer comprising material of any of embodiment 8, which comprises less than 35 wt % of component c) and/or less than 20 wt % of component d) more preferably less than 20 wt % of component c) and/or less than 20 wt % of component d), most preferably less than 17 wt % for c) and/or d), more preferably about 8 to 17 wt % for c) and/or d).

Preferably such a biomaterial contains about equal amounts of component c) and d), preferably the component c) and d) together does not rise above 40 wt %.

Furthermore, such a biomaterial contains preferably less than 40 wt % of the polymer, more preferably less than 30 wt %, even more preferably less than 25 wt %, most preferably between 20 and 25 wt %.

More preferably the synthetic biomaterial of the above embodiments comprises a second polymer, which is a solid polymer.

10. The polymer comprising material of any of embodiments 8 or 9, wherein the second polymer is a water soluble solid polymer, preferably a polyethylene glycol, more preferably PEG 1500.

Preferably the amount of the solid polymer is less than 8 w %, more preferably less than 5 wt %, even more preferably less than 3 wt %, most preferably between 1 and 2.5 w %.

11. The polymer comprising material of any of embodiments 1 to 10, comprising an active agent, which is preferably a protein or peptide, preferably a growth factor, preferably a bone morphogenetic protein, more preferably a periodontal ligament, cementum and/or alveolar bone inducing agent, most preferably GDF-5.

12. A method for treating a water binding agent comprising (a) milling and/or sieving of the water binding agent, preferably wet milling of the water binding agent to reduce the particle size, (b) drying or burning of the water binding agent under conditions to obtain a crystal water binding agent and to maintain the water binding capacity of the agent, preferably between 180° C. to 500° C., preferably between 180° C. and 200° C.

Such method can be used with any water binding agent of the present invention as listed above and water binding agents treated in this manner are preferred in this invention.

13. A method for manufacturing a material of embodiments 2 to 11 comprising (a) drying of the starting compounds;

(b) milling and/or sieving of the water binding agent to reduce the particle size, preferably by wet milling; and/or (c) drying or burning of the water binding agent under conditions to obtain a crystal water binding agent and to maintain the water binding capacity of the agent, preferably between 180° C. to 500° C., preferably between 180° C. and 200° C.; and (d) optionally drying the biomaterial under reduced pressure at ambient temperature followed by venting with dry nitrogen preferably in a freeze dryer prior packaging.

14. A kit using the material of embodiments 2 to 11, the kit comprising (a) a first receptacle preferably adopted to house at least one active agent (b) a second receptacle comprising the biomaterial of claims 2 to 11.

Amend line 8 on page 28 of the specification to read:

(b) a second receptacle comprising the biomaterial of embodiments claims 2 to 11.

15. Use of the material of any of embodiments 2 to 11 for the preparation of a pharmaceutical composition for treatment of cartilage and/or bone defects, critical size defects, full thickness defects, non-union fracture, periodontitis, peri-implantitis, sinus-floor augmentation, maxillo-facial intrabony defects preferably periodontitis, preferably while preventing formation of ankylosis.

16. Use of a water binding agent for inhibiting water induced polymer degradation in a polymer comprising material, wherein the water binding agent is not removed prior to application of the material.

17. Use of a water binding agent for inducing blood clot formation or blood clot stabilization in a polymer comprising material, wherein the water binding agent is not removed prior to application of the material.

Preferably, blood clot formation or blood clot stabilization is induced in a polymer comprising material upon in situ hardening in a bleeding tissue.

18. Use of a water binding agent for increasing storage stability in a polymer comprising material, wherein the water binding agent is not removed prior to application of the material.

19. A stable packaging system comprising the polymer comprising material of claim 1 and a package, wherein the system is stable for more than one month, more than three month, more than 6 month or more than one year.

EXAMPLES

Example 1

Manufacturing of Formulations A-D of FIG. 1-3

Four different formulations (materials) were manufactured: Formulation A without a water binding agent according to the present invention, formulation B to D, where part of the inorganic filler (in this example beta-tricalcium phosphate (β-TCP)) was exchanged by different amounts of calcium sulphate anhydrous. The formulations used were composed as follows:
Formulation A
  beta-tricalcium phosphate powder (33.3 wt %), poly(lactic-co-glycolic-acid) with a lactic-/glycolic acid ratio of 50:50 and a molecular weight of 25000 g mol-1 (22.2 wt %), polyethylene glycol 400 (44.5 wt %)
Formulation B
beta-tricalcium phosphate powder (29.2 wt %), poly(lactic-co-glycolic-acid) with a lactic-/glycolic acid ratio of 50:50 and a molecular weight of 25000 g mol-1 (22.2 wt %), polyethylene glycol 400 (44.5 wt %) and calcium sulphate anhydrous (4.2 wt %)
Formulation C
  beta-tricalcium phosphate powder (25.0 wt %), poly(lactic-co-glycolic-acid) with a lactic-/glycolic acid ratio of 50:50 and a molecular weight of 25000 g mol-1 (22.2 wt %), polyethylene glycol 400 (44.5 wt %) and calcium sulphate anhydrous (8.3 wt %)
Formulation D
  beta-tricalcium phosphate powder (20.8 wt %), poly(lactic-co-glycolic-acid) with a lactic-/glycolic acid ratio of 50:50 and a molecular weight of 25000 g mol$^{-1}$ (22.2 wt %), polyethylene glycol 400 (44.5 wt %) and calcium sulphate anhydrous (12.5 wt %)

Initially either b-TCP-powder (formulation A) or b-TCP-powder and calcium sulphate dihydrate ($CaSO_4*2H_2O$) (formulation B-D) were levigated and sieved to obtain a particle size ranged between 25-150 μm. Subsequently these two components were heated at 300° C. for 2 h to reduce their content of water. Concurrently polyethylene glycol 400 (PEG 400) was pre-dried for 24 h applying a molecular sieve. To prepare the biomaterial, the poly(-lactic-co-glycolic-acid) polymer (Resomer® RG503H purchased by Boehringer Ingelheim) was added to the obligate amount of organic solvent (PEG 400) in a porcelain crucible. These two components were homogenized and were heated at a temperature of approximately 80° C. until the polymer was completely dissolved in the organic solvent. Subsequently the inorganic fillers (beta-tricalcium phosphate and optionally calcium sulphate dihydrate) were dispersed in the polymeric solution. Said polymeric solution was filled up in 6R-glass vials which were locked with rubber stoppers. Finally the formulation was subjected to an isothermal drying step (0.2 mbar, 35° C., 3 h). Afterwards the vials containing the dried preparations were locked under nitrogen atmosphere.

The formulation prepared was stored at 37° C. within an evacuated exsiccator to prevent external water from diffusing in the primary packing material.

In this example calcium sulfate anhydrous was used as a water-binding agent. Alternatively, instead of calcium sulfate anhydrous other water binding agents according to the present invention such as sodium sulfate anhydrous, magnesium ethanolate or zeolite can be used.

Example 2

Manufacturing of Formulation E

The biomaterial was manufactured as follows (E1): Initially calcium sulphate anhydrous 15.0 wt % (prepared as described under Example 1) and the organic solvent polyethylene glycol 300 47.0 wt % were homogenized using an agate-mortar with pestle. This suspension was added to polymer (RG502H; PLGA; polymer composition: 48-52 mol % D,L-Lactide and 48-52 mol % Glycolide; inherent viscosity: 0.16-0.24 dl/g, 25° C., 0.1% in $CHCl_3$; (RESOMER® Boehringer Ingelheim)) 20.0 wt %, carboxymethlycellulose sodium salt 3.0 wt %, D(−)-Mannitol 13.0 wt %, and polyethylene glycol 1500 2.0 wt %, in a porcelain crucible. The suspension comprising of the inorganic filler and the organic solvent, and the excipients were homogenized and heated at a temperature of approximately 80° C. until the polymer was completely solved in the organic solvent whereas the non-soluble excipients were dispersed in the polymeric solution. The polymer paste was transferred into an appropriate packaging material (e.g. PP or glass syringe).

E2 was prepared without Mannitol comprising RG502H 20.0 wt %, polyethylene glycol 300 51.0 wt %, calcium sulphate anhydrous 18.0 wt % (prepared as described under Example 1), carboxymethlycellulose sodium salt 3.0 wt %, and polyethylene glycol 1500 5.0 wt %.

E3 was prepared without Mannitol and PEG 1500 comprising RG502H 24.0 wt %, polyethylene glycol 300 52.0 wt %, calcium sulphate anhydrous 18.0 wt % (prepared as described under Example 1), carboxymethlycellulose sodium salt 3.0 wt %, and alpha-tocopherol 3.0 wt %.

Example 3

Manufacturing of the Active Agent Lyophilizate

The active agent lyophilizate (0.6 wt %) was manufactured as follows: Initially the obligate amount of acetic acid was pipetted to the stock solution of rhGDF-5 (2.8 mg/ml in 10 mM HCl) leading to a final concentration of 50 mM and a pH of 3.0±0.2. In an second step the protein solvent was equimolar neutralised using 1 M NaOH. The required amounts of D(+)-Trehalose (16.6 wt %), D(−)-Mannitol (66.2 wt %) were dissolved in $H_2O$ within a specially designed glass vials with a small volume inlay (MGlas AG) and the affordable amount of acetic acid (9.9 wt %) was pipetted resulting in a final concentration of 50 mM. To prepare the final formulation, the active agent solution was diluted to 0.7 mg/ml with 50 mM acetic acid and added to the dissolved bulking materials. After closing of the glass vials with rubber stoppers, the solution was lyophilized. Alternatives can be prepared in analogy.

Example 4

Manufacturing of Formulation F

The biomaterial containing the biomaterial of Example 2 and the drug lyophilizate of Example 3 was prepared as follows: After removing of the rubber stopper from the specially designed glass vial with a small volume inlay, the entire volume of the polymer paste (Example 1) within the PP or glass syringe was injected into the glass containing the drug lyophilizate (Example 3). 99, 4 wt % of Example 2 and 0.6 wt % of Example 3 were admixed using a spatula to obtain a homogeneous entity and to minimize the loss of material, and the final biomaterial was refilled in the same syringe.

Example 5

Investigation of the Molecular Weight of the Polymer by Combination of Gel Permeation Chromatography (GPC) and Multi-Angle-Laser-Light-Scattering (MALLS)

Method A (used for FIG. 6): Initially 100-150 mg of the biomaterial of Example 1 were dissolved in 1 ml of tetrahydrofuran (THF). The insoluble inorganic materials were removed via centrifugation (13000 $min^{-1}$, 5 minutes). The supernatant containing the poly(lactic-co-glycolic-acid) and PEG 400 was evaporated yielding a residue composed of poly(lactic-co-glycolic-acid) dissolved in PEG 400. To remove the latter, the residue was mixed with 1 ml of aqua bidest, what led to the precipitation of the poly(lactic-co-glycolic-acid). Subsequently the supernatant was rejected and the solid residue consisting of the pure PLGA-copolymer was vacuum dried.

To analyze the polymer via GPC-MALLS the isolated polymer had to be dissolved in THF adjusting a concentration of approximately 10 mg/ml. For molecular weight determination, the following conditions were adopted: THF was the mobile phase at a flow rate of 1 ml/min and ambient temperature. For the chromatographic separation of the samples a Phenogel 5u MXL GPC column (size 300*7.80 mm, Phenomenex®) was used. The detection was carried by serially coupled UV-, MALLS- and RI detectors. The refractive index increment (dn/dc) of Resomer® RG 503H was determined to be 0.045 by applying a polystyrene standard ($M_w$ 34 kDa) for calibration. The injection volume added up to 25 µl.

Method B (used with Example 1 for FIG. 7): Biodegradation studies of the injectable composite were performed by in-vitro incubation of the composite in phosphate buffered saline for four weeks at 37° C. At each analytical time point, specimens were dried for mass balance and afterwards solubilized in tetrahydrofuran anhydrous (Merck, Darmstadt, Germany) for gel permeation chromatography (GPC) to determine the weight average polymer molecular weight of PLGA. Narrow molecular weight polystyrenes in the range of 5.6-34.0 kDa (PSS, Mainz, Germany) were used as standards. The GPC conditions were as follows: Tosoh TSKgel G3000HHR (5 µm, 7.8 mm×30 cm) column (Tosoh Biosciences, Stuttgart, Germany) maintained at 40° C., Dionex P580 series isocratic pump, autosampler, column oven (Dionex Corp., Sunnyvale, Calif., USA), miniDAWN™ multi-angle laser light scattering detector (Wyatt Technology Corp., Santa Barbara, Calif., USA), RI 2000-F refractive index detector (Schambeck SFD, Bad Honnef, Germany), and 80 µl injection volume. Tetrahydrofuran at a flow rate of 1 ml/min was used as the mobile phase. The average molecular weight (Mw) was calculated by Astra® GPC software (Wyatt Technology Corp., Santa Barbara, Calif., USA). The relative molecular weight was expressed as percentage of the Mw of the sample to the initial Mw of PLGA within the injectable composite.

Example 6

Mechanical Testing

The biomaterial, prepared as described in Example 1 was transferred into wells of a 96-well plate (150-200 mg per well, three wells per time point and sample). Subsequently the well plate containing the samples was transferred into an incubation bath, which was constantly remained at 37° C. to simulate physiological conditions, whereas PBS-buffer served as an incubation media. After 24 h of incubation the 96-well plate was removed from the incubation bath to carry out the mechanical testing.

Hardness of the specimens was tested by using a TH 2730 (Fa Thuemler). Substantially this machine consists of a metallic punching tool, which enables to apply compressive forces on the specimens and a LVDT-transducer, which serves to control and to measure the applied force and to determine the distance, covered during the measurement. Prior to testing the different specimens, the height ($h_1$) of a well, which does not contain any specimen has to be defined. Therefore the starting point of the punching tool for the following measurements was fixed. The actual determination of hardness of the specimens encompasses two steps. In a first measurement the height of the particular specimen ($h_2$) has to be ascertained, whereas the crosshead velocity of the punching tool was 40 mm per minute and the applied force was limited to 0.2 N. A second measurement was carried out to determine the distance (d), covered by the punching tool within the specimen during a period of 30 seconds, whereby the applied force was kept constant at 20 N. Hardness of the specimen was calculated in the following manner:

$$\text{hardness } [\%] = (h_2-d)/h_2 * 100\%$$

The method described was based on the determination of hardness according to Shore (DIN 53505).

Example 7

Determination of Over all Water Content Via Karl Fischer Titration (Method 1)

Approximately 50 mg of the biomaterial of Example 1 and 2 respectively were accurately weight in a 6R-glass vial and were transferred in the oven associated with the titration vessel. The temperature of the oven was adjusted to 140° C. The water contained in the test samples was driven out by a constant nitrogen flow and was so transferred to the titration vessel.

The water content was calculated using the following equation:

$$\text{water content } (\%) = \frac{W_{s\ overall}}{M_0} * 100$$

Where $W_{s\ overall}$ is the mass of water in the sample, $M_0$ is the initial weight of the biodegradable paste

Example 8

Determination of the Content of Free Water Via Karl Fischer Titration (Method 2)

Approximately 50 mg of the biomaterial of Example 1 and 2 respectively were accurately weight in a 6R-glass vial. Subsequently 1.0 ml of anhydrous methanol was added. The samples were then incubated for 1 h. Afterwards 100 µl of the samples were withdrawn from the vials using a syringe and were injected into the titration vessel. The water content was calculated using the following equation:

$$\text{water content (\%)} = \frac{W_s - W_b}{M_0} * 100$$

Where $W_s$ is the mass of water in the sample, $W_b$ is the mass of water in methanol and $M_0$ is the initial weight of the biodegradable paste material [according to Journal of Controlled Release 108, 2005, 1-9]

Example 9

Preparation for SEM-Analysis

The porosity of the injectable composite after application was evaluated by in-vitro incubation in phosphate buffer at 37° C. and upon drying for 24 hours at 4° C. analyzed by scanning electron microscopy. For SEM investigation, samples were sputtered with gold by using an Edwards S150B sputter coater (Edwards, Crawley, West Sussex, England). The gas pressure was 6 mbar, the current was 10 mA, the voltage was 1.5 kV, and the coating time was 90 s. SEM analysis of samples was performed by means of a LEO 1455 (Carl Zeiss Inc., Thornwood, N.J., USA) at 10 kV.

Example 10

Preparation of Cryo-Sections for Histology and LM-Analysis

After incubation of the biomaterial of Example 2 in human whole blood at 37° C. for 12 hours, the hardened specimens embedded in the formed blood clot were primed and transferred into PEEL-A-WAY Tissue Embedding Molds using Tissue Freezing Medium on dry-ice. 12 µm cryo-sections were prepared followed by standard hematoxylin nucleus staining, ethanol fixation, and Immumount mounting prior to light microscopy analysis at the blood clot biomaterial interface.

Example 11

Preclinical One-Wall Intrabony Periodontal Defect Model in the Beagle Dog

The biocompatibility and efficacy of the biomaterial with and without 1 µg, 20 µg and 100 µg rhGDF-5 (Example 2 and 4) for the treatment of periodontal osseous defects was analyzed in a preclinical one-wall intrabony periodontal defect model in the Beagle dog. For this purpose the biomaterials were implanted into surgically created bilateral, critical-size, one-wall, intrabony periodontal defects in the Beagle dog (Kim, C-S., Choi, S-H., Chai, J-K., Cho, K-S., Moon, I-S., Wikesjö, U. M. E., Kim, C-K. (2004) J Periodontol 75: 229-235). The biomaterials were implanted into the "box type" defects and the defect sites were closed with mucoperiosteal flaps and sutured to allow primary intention healing. The defects were allowed to heal for 8 weeks followed by histologic and histometric analysis. The histometric parameters were as follows: defect height (DH), junctional epithelium (JE), connective tissue adhesion (CT), cementum regeneration (NC), and bone regeneration (NB).

Example 12

Manufacturing of Formulation G Comprising a Biodegradable Polymer and an Organic Solvent Initially the obligate amount (66.6 wt %) of predried polyethylene glycol 400 (the drying procedure of this component was performed according to Example 1) is weight in an porcelain crucible. Subsequently the respective amount of Resomer® RG 503H was added by homogenizing the two components by means of a spatula. Thereby the two components were heated at a temperature of approximately 80° C. until the polymer was completely solved in the organic solvent.

Example 13

Differential Scanning Calorimetry Analysis (DSC)

Thermal analysis of samples were performed by using a Phoenix differential scanning calorimetry (DSC) system (Netzsch) equipped with a DSC 204 cell, a TASC 414/3A heating controller, and a CC 220L cooling controller. The cooling was carried out by means of liquid nitrogen. Samples weighing 10-20 mg were sealed in an aluminum pan with punched cap. An empty sealed aluminum pan was used as the reference. Both the reference pan and the sample pan were allowed to equilibrate isothermally. The heating and cooling rates ranged between 10 and 30 K/min. Two heating scans were performed, whereas the first one was used to eliminate any sample history and the second one served for analysis. The glass transition temperature (Tg) of the samples was analyzed by Proteus-Thermal Analysis software (Netzsch).

The invention claimed is:
1. A method for manufacturing a polymer-comprising material comprising
   (i) a plasticizer, which is a water soluble or water miscible organic solvent,
   (ii) a water degradable and water insoluble polymer, wherein the polymer is soluble in the plasticizer and capable of solidifying in an aqueous medium or body fluid to form a solid or semi-solid implant upon removal of the plasticizer into the surrounding tissue, and
   (iii) a water-binding agent, wherein the water-binding agent is present in an amount of 25 wt % or less, which amount is sufficient to physically absorb and/or adsorb or chemically adsorb water to prevent degradation of the polymer, and wherein the water-binding agent is silica gel, zeolite, dewatered calcium sulfate dehydrate, calcium sulfate anhydrous, sodium sulfate anhydrous, magnesium sulfate anhydrous, magnesium ethanolate, calcium ethanolate, aluminum ethanolate, or a mixture thereof,
which method comprises
   (a) drying the plasticizer,
   (b) milling and/or sieving the water-binding agent to reduce particle size,
   (c) drying or burning the water-binding agent such that the water-binding agent maintains its water binding capacity, and
   (d) mixing the plasticizer, the water-binding agent, and the polymer.
2. A kit comprising
   (a) a first receptacle to house at least one active agent, and
   (b) a second receptacle comprising a the polymer-comprising material comprising
   (i) a plasticizer, which is a water soluble or water miscible organic solvent,
   (ii) a water degradable and water insoluble polymer, wherein the polymer is soluble in the plasticizer and capable of solidifying in an aqueous medium or body fluid to form a solid or semi-solid implant upon removal of the plasticizer into the surrounding tissue, and

(iii) a water-binding agent, wherein the water-binding agent is present in an amount of 25 wt % or less, which amount is sufficient to physically absorb and/or adsorb or chemically adsorb water to prevent degradation of the polymer, and wherein the water-binding agent is silica gel, zeolite, dewatered calcium sulfate dehydrate, calcium sulfate anhydrous, sodium sulfate anhydrous, magnesium sulfate anhydrous, magnesium ethanolate, calcium ethanolate, aluminum ethanolate, or a mixture thereof.

3. A method for inducing blood clot stabilization in an animal, which comprises applying a polymer-comprising material to the animal, wherein the polymer-comprising material comprises
(i) a plasticizer, which is a water soluble or water miscible organic solvent,
(ii) a water degradable and water insoluble polymer, wherein the polymer is soluble in the plasticizer and capable of solidifying in an aqueous medium or body fluid to form a solid or semi-solid implant upon removal of the plasticizer into the surrounding tissue, and
(iii) a water-binding agent, wherein the water-binding agent is present in an amount of 25 wt % or less, which amount is sufficient to physically absorb and/or adsorb or chemically adsorb water to prevent degradation of the polymer, wherein the water-binding agent is silica gel, zeolite, dewatered calcium sulfate dehydrate, calcium sulfate anhydrous, sodium sulfate anhydrous, magnesium sulfate anhydrous, magnesium ethanolate, calcium ethanolate, aluminum ethanolate, or a mixture thereof, and wherein the water-binding agent is not removed prior to the application of the material.

4. A method of treating a disorder in an animal, which method comprises administering an effective amount of a pharmaceutical composition comprising an active agent and a polymer-comprising material, wherein the polymer-comprising material comprises
(i) a plasticizer, which is a water soluble or water miscible organic solvent,
(ii) a water degradable and water insoluble polymer, wherein the polymer is soluble in the plasticizer and capable of solidifying in an aqueous medium or body fluid to form a solid or semi-solid implant upon removal of the plasticizer into the surrounding tissue, and
(iii) a water-binding agent, wherein the water-binding agent is present in an amount of 25 wt % or less, which amount is sufficient to physically absorb and/or adsorb or chemically adsorb water to prevent degradation of the polymer, and wherein the water-binding agent is silica gel, zeolite, dewatered calcium sulfate dehydrate, calcium sulfate anhydrous, sodium sulfate anhydrous, magnesium sulfate anhydrous, magnesium ethanolate, calcium ethanolate, aluminum ethanolate, or a mixture thereof,
to an animal that has a disorder selected from the group consisting of: cartilage and/or bone defects, critical size defects, full thickness defects, non-union fracture, periodontitis, periimplantitis, sinus-floor augmentation, maxillo-facial intrabony defects, periodontittis, and ankylosis, whereupon the disorder is treated in the animal.

5. The method of claim 1, wherein the polymer-comprising material further comprises an inorganic filler, a pore forming agent, a pore initiating filler, or at least a second polymer or any combination thereof.

6. The method of claim 5, wherein the second polymer is a water soluble solid polymer.

7. The kit of claim 2, wherein the polymer-comprising material further comprises an inorganic filler, a pore forming agent, a pore initiating filler, or at least a second polymer or any combination thereof.

8. The kit of claim 7, wherein the second polymer is a water soluble solid polymer.

9. The method of claim 3, wherein the polymer-comprising material further comprises an inorganic filler, a pore foaming agent, a pore initiating filler, or at least a second polymer or any combination thereof.

10. The method of claim 9, wherein the second polymer is a water soluble solid polymer.

11. The method of claim 4, wherein the polymer-comprising material further comprises an inorganic filler, a pore forming agent, a pore initiating filler, or at least a second polymer or any combination thereof.

12. The method of claim 11, wherein the second polymer is a water soluble solid polymer.

* * * * *